(12) United States Patent
Potti

(10) Patent No.: US 6,440,149 B1
(45) Date of Patent: Aug. 27, 2002

(54) TONGUE AND TOOTH CLEANING DEVICE

(76) Inventor: Dasan Potti, 27104 Patriot Dr., Salisbury, MD (US) 21801

( * ) Notice: Subject to any disclaimer, the term of this patent is extended or adjusted under 35 U.S.C. 154(b) by 0 days.

(21) Appl. No.: 09/840,559

(22) Filed: Apr. 23, 2001

(51) Int. Cl.⁷ .............................................. A61B 17/24
(52) U.S. Cl. ...................................................... 606/161
(58) Field of Search ................................ 606/160, 161; 132/323–328; D4/108

(56) References Cited

U.S. PATENT DOCUMENTS

| 1,080,929 | A | * | 12/1913 | Romeo | |
|---|---|---|---|---|---|
| 2,517,806 | A | * | 8/1950 | Streiler | |
| 2,735,436 | A | | 2/1956 | Russo | |
| D221,036 | S | | 6/1971 | Potti | |
| 4,041,962 | A | | 8/1977 | Johansson et al. | |
| 4,192,330 | A | * | 3/1980 | Johnson | |
| D276,088 | S | | 10/1984 | Fong | |
| 4,790,336 | A | | 12/1988 | Kuo | |
| 4,906,566 | A | | 3/1990 | Cillimore et al. | 435/34 |
| 5,097,852 | A | * | 3/1992 | Wu | 132/323 |
| 5,184,719 | A | * | 2/1993 | Gordon | 132/323 |
| 5,202,262 | A | | 4/1993 | Lemonnier | 435/299 |
| D338,084 | S | | 8/1993 | Potti | |
| 5,340,747 | A | | 8/1994 | Eden | 436/172 |
| 5,356,815 | A | | 10/1994 | Ciotti | 435/291 |
| 5,438,726 | A | | 8/1995 | Leite | |
| D374,744 | S | | 10/1996 | Dolan et al. | |
| 5,643,743 | A | | 7/1997 | Chang et al. | 435/34 |
| 5,735,298 | A | | 4/1998 | Mayne et al. | |
| 5,845,358 | A | | 12/1998 | Woloch | |
| D408,534 | S | | 4/1999 | Jansheski | |
| 5,916,228 | A | * | 6/1999 | Ripich et al. | 606/161 |
| 5,967,152 | A | * | 10/1999 | Rimkus | 606/161 |
| 6,006,762 | A | * | 12/1999 | Hsia | 132/327 |
| 6,022,698 | A | | 2/2000 | Chen et al. | 435/24 |
| 6,051,394 | A | | 4/2000 | Simmons et al. | 435/29 |
| 6,056,763 | A | * | 5/2000 | Parsons | 606/161 |
| 6,083,235 | A | | 7/2000 | Wagner | |
| 6,171,323 | B1 | | 1/2001 | Potti et al. | |

FOREIGN PATENT DOCUMENTS

| WO | 9714034 | 4/1997 |
|---|---|---|
| WO | 9853301 | 11/1998 |
| WO | 0023189 | 4/2000 |

* cited by examiner

Primary Examiner—Michael J. Milano
Assistant Examiner—Tan-uyen T. Ho
(74) Attorney, Agent, or Firm—Hodgson Russ LLP

(57) ABSTRACT

A tongue and tooth cleaning device for cleaning the surface of a tongue and cleaning between teeth comprising a handle having a scraping end, the scraping end having a scraper, the scraper for removing from the tongue when scraped along the tongue. Further, the scraper has a toothed edged inner scraper blade for disturbing and breaking up debris lodged on the tongue, and a smooth edged outer scraper blade for scraping the debris off the tongue. The other end of the handle has a floss holding assembly having fork-shaped tines for holding floss therebetween.

23 Claims, 3 Drawing Sheets

TONGUE AND TOOTH CLEANING DEVICE

BACKGROUND

Most people brush their teeth perhaps once a day and floss between their teeth perhaps twice a week.

Then there are the diligent people who brush their teeth one or more times a day and floss at least once a day. Mouthwashes and chewing gum are also used in attempts to "freshen breath" and suppress the growth of bacteria in the mouth.

However, even with all of these devices, tools, washes, and products, people who brush daily and attempt to maintain healthy oral hygiene still develop cavities, gum ailments, such as gingivitis, unpleasant breath, and tooth decay. There are devices that offer additional means by which a person can attempt to preserve their oral hygiene, but these devices are oftentimes cumbersome and difficult to use. Hence, to date, there is no device that satisfactorily provides a reliable, easy to use, means to thoroughly clean the tongue and the teeth.

SUMMARY

The present invention overcomes the problems associated with prior oral hygiene devices. The tongue and tooth cleaning device described herein satisfies the long felt need for an easy to use and effective way to remove debris from the tongue and from the spaces between the teeth.

The tongue and tooth cleaning device has a handle having a scraping end, the scraping end having a scraper, the scraper for removing debris from the surface of the tongue when scraped along the tongue. The debris includes bacteria and food particles. In order to accomplish such scraping, the scraper further comprises a scraper head having a toothed edged inner scraper blade for disturbing debris on the tongue, and a smooth edged outer scraper blade for cleanly scraping the debris off the tongue. This dual bladed action provides significant cleaning of the tongue.

The device further comprises a flossing end positioned on the handle opposite to the scraping end, the flossing end for holding floss. The handle defines a longitudinal axis passing through the length thereof, and the flossing end has a floss holding assembly. The floss holding assembly lies in the plane that the handle lies, and has fork-shaped tines that point in a direction perpendicular to the longitudinal axis of the handle. The fork-shaped tines comprise a proximate tine and a distal tine, these tines each have a groove for holding floss therein.

Thus, the device thoroughly cleans the user's tongue, and the spaces between the user's teeth.

FIGURES

DESCRIPTION

Figure 1:
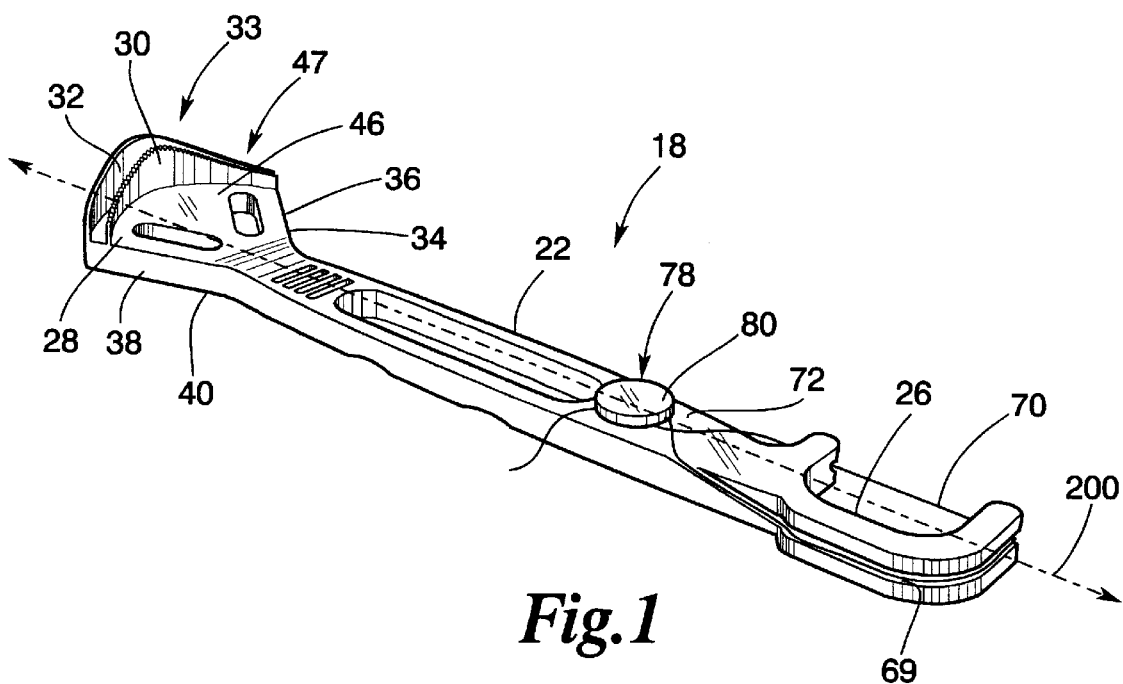
FIG. 1 is a bottom perspective view of the tongue and tooth cleaning device showing the bottom surface thereof.
Figure 2:
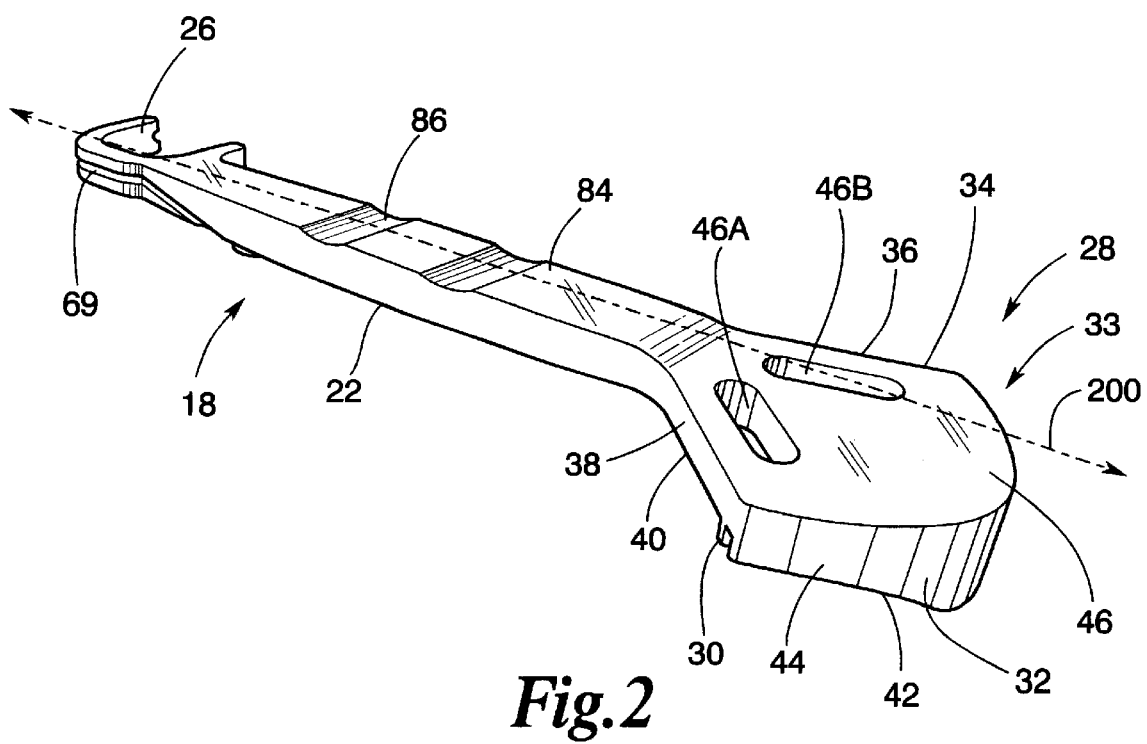
FIG. 2 is a top perspective view of the tongue and tooth cleaning device showing the top surface thereof.
Figure 3:
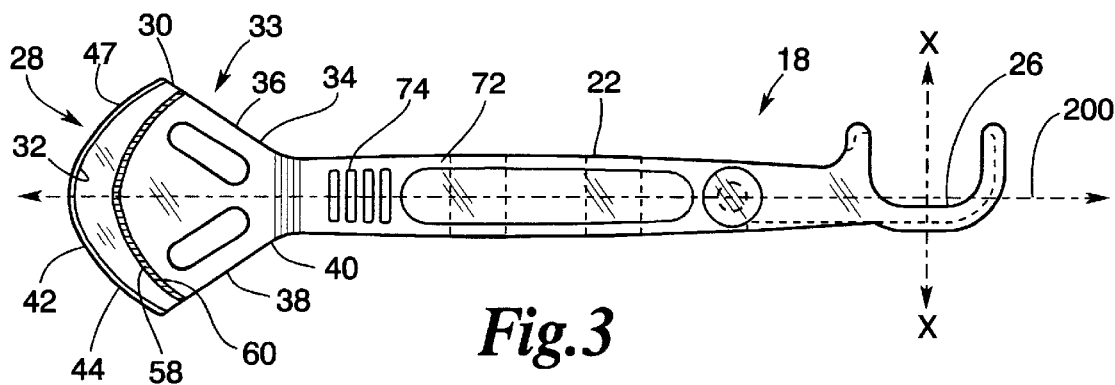
FIG. 3 is a bottom plan view of the tongue and tooth cleaning device.
Figure 4:
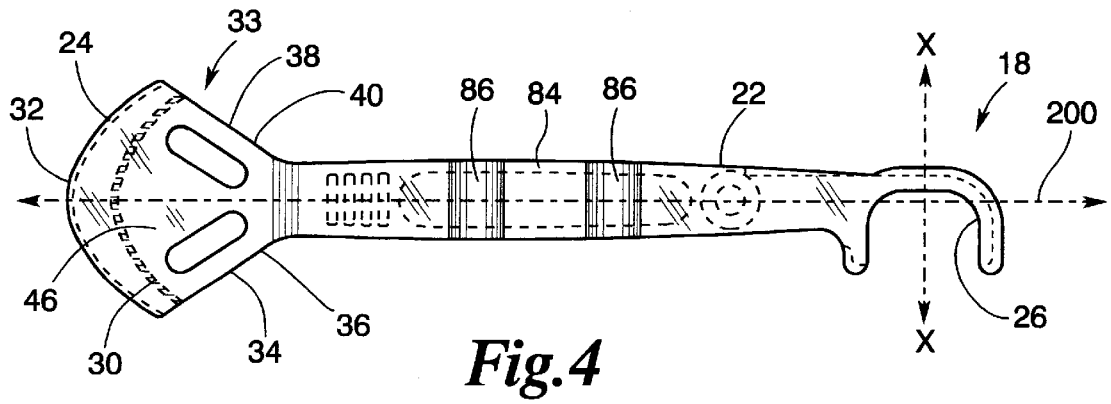
FIG. 4 is a top plan view of the tongue and tooth cleaning device.
Figure 9:
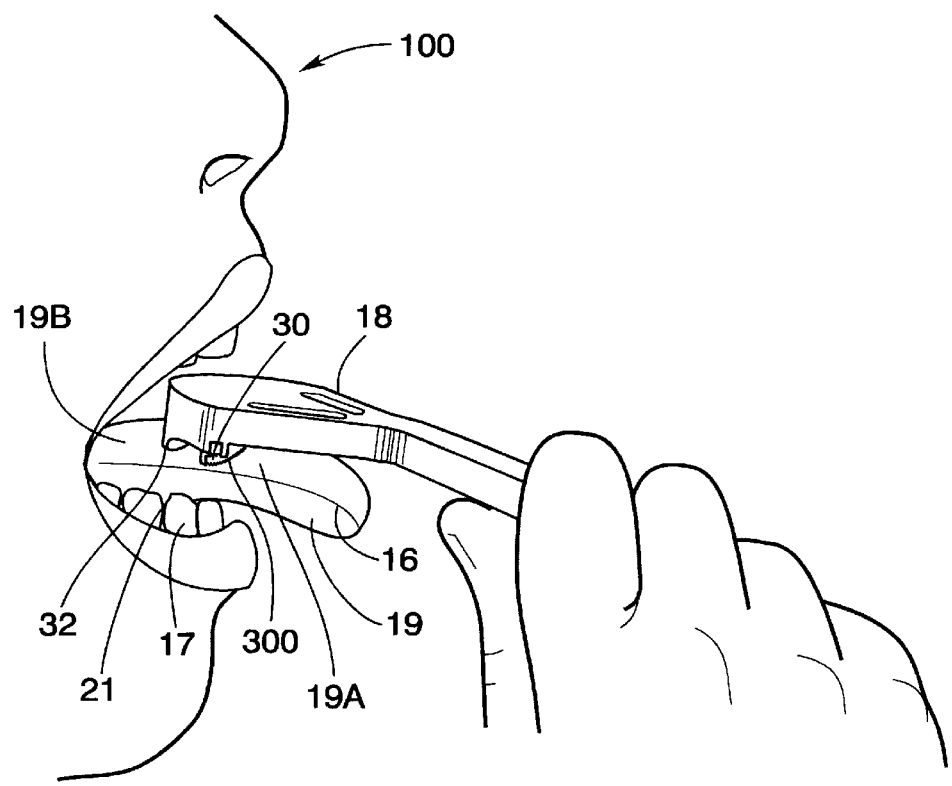
FIG. 9 is a view of the tongue and tooth cleaning device being used by a user.

Turning now to FIG. 1, shown therein is a bottom perspective view of the tongue and tooth cleaning device 18. The tongue and tooth cleaning device 18 (hereinafter device 18) is for cleaning the surface of the tongue 19A (the tongue 19 is shown in FIG. 9), and the spaces 21 between the teeth 17. The device 18 has a handle 22 having a scraping end 24 at one end thereof, and a flossing end 26 at the other end thereof. As seen on FIG. 1, the scraping end 24 and flossing end 26 are at opposite ends of the handle 22. The longitudinal axis (designated 200 in the FIGS.) of the device 18 passes lengthwise through the handle 22, as seen in FIGS. 2–4.

Figure 5:
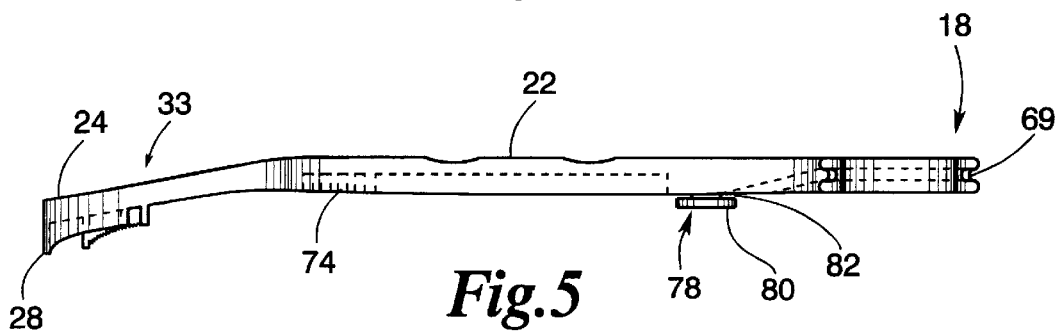
FIG. 5 is a front side elevational view of the tongue and tooth cleaning device.

The scraping end 24 of the handle 22 has a scraper 28 extending therefrom. The scraper 28 is for removing debris 300 from the tongue 19 when scraped along the tongue 19. The scraper 28 is at an angle to and bent towards the bottom surface 72 of the handle 22, as seen in FIGS. 1, 2, and 5. At the other end of the handle 22 is the flossing end 26 of the device 18, as seen in FIGS. 1–4, comprising the floss holding assembly 62. The flossing end 26 is for holding floss 70, the floss is for cleaning the spaces 21 between the teeth 17, these spaces 21 are shown in FIG. 9.

A detailed description of the scraping end 24 of the device 18 is now presented. As seen in FIGS. 1–4, the scraper end 24 has scraper 28 extending therefrom, the scraper 28 having a scraper head 33. At least two of scraper blades 47 protrude from the bottom surface 72 of the device 18. As seen in FIG. 1, the scraper head 33 has a scraper head flat surface 46 from which the plurality of scraper blades 47 protrude, these blades include the toothed edged inner scraper blade 30 and smooth edged outer scraper blade 32 (hereinafter blades 35 30,32). The blades 30,32 are proximate or adjacent to one another as seen in FIG. 1, and as described below, this configuration of the blades 30,32 thoroughly removes debris 300 from the user's 100 tongue 19.

The scraper head 33 is defined by a first edge 34 long the first side thereof 36, a second edge 38 along a second side 40 thereof, and a third edge 42 along the third side thereof 44. It is noted that in the figures, third edge 42 and third side 44 are shown as being curved, but in other embodiments third edge 42 edge and third side 44 may be straight. Similarly, in FIGS. 1 and 2, the first edge 34 and first side 36, and second edge 38 and second side 40 are shown as straight, but may be embodied as curved, or in other shapes well known to those of ordinary skill in the art.

The scraper head flat surface defines cutouts 46a and 46b therein. The toothed edged inner scraper blade 30 has a plurality of scraping teeth 58, and has a width designated w1 (FIG. 7) at the first edge 34 of the first side 36 of the scraper head 33. The toothed edged inner scraper blade 30 has a width designated w2 (FIG. 7) at the second edge 38 of the second side 40 of the scraper head 33, w2 being equal to w1. The width w1 and the width w2 each increase, as the toothed edged inner scraper blade 30 approaches the longitudinal axis of the device 18, the longitudinal axis of the device indicated by reference number 200 in the FIGS. The longitudinal axis of the device 200 passes lengthwise through the handle 22 of the device 18. The widths w1 and w2 reach their maximum inner blade protrusion (wmax-inner) 49 at the location where the longitudinal axis 200 of the device 18 passes through the toothed edged inner scraper blade 30. This is shown in FIGS. 2, 3 and 4.

Similarly, the smooth edged outer scraper blade 32 protrudes from the scraper head flat surface 46 from the bottom surface 72 of the device 18, as seen in FIGS. 1, 2, 3 and 6. The smooth edged outer scraper blade 32 has a width designated w3 (FIG. 6) at the first edge 34 of the first side 36 of the scraper head 33. The smooth edged outer scraper blade 32 has a width designated w4 (FIG. 6) at the second edge 38 of the second side 40 of the scraper head 33, w3 being equal to w4. The width w3 and w4 each increase, as the smooth edged outer scraper blade 32 approaches the longitudinal axis 200 of the device 18. The widths w3 and w4 reach their maximum outer blade protrusion (wmax-outer) 55 at the location where the longitudinal axis 200 of the device 18 passes through the smooth edged outer scraper blade 32. This is shown in FIGS. 1–4.

As seen in FIGS. 1, 2, and 5–7, w1 is equal to w2, and w3 is equal to w4. Further, in this embodiment, wmax-inner 49 is less than wmax-outer 55, as seen in FIGS. 1 and 5. A reason for wmax-inner 49 being less than wmax-outer 55 in this embodiment is so that when the device 18 is pulled (scraped or dragged) by the user 100 (FIG. 9) across the surface of the tongue 19A (from the back of the throat to the tip of the tongue 19 as seen in FIG. 9), the toothed edged inner scraper blade 30 breaks up and dislodges debris 300 from the tongue 19. The debris 300 includes food particles, bacteria, and other undesirable materials known to accumulate on the tongue, such materials well known to those of ordinary skill in the art. As the pulling continues, the smooth edged outer scraper blade 32 then follows, so as to cleanly scrape off all the materials and debris 300 that were dislodged by the toothed edged inner scraper blade 30. This two bladed process of scraping, wherein a smooth edged outer scraper blade 32 follows immediately behind a toothed edged inner scraper blade 30, leaves the user's 100 tongue 19 much cleaner then it was prior to scraping.

It is noted that in the present embodiment, the toothed edged inner scraper blade 30 and the smooth edged outer scraper blade 32 are curved, the degree of curvature mimicking the degree of curvature of the curved side 44 of the scraper head 33, as seen in FIGS. 1 and 3. This U-shaped curvature (or substantially V-shaped configuration), as more fully described below, promotes the scraping and gathering of debris 300 off the user's 100 tongue 19. In other embodiments however, the smooth edged outer scraper blade 32 and the toothed edged inner scraper blade 30 may be embodied to have no curvature. Further, the shapes 59 of each of the plurality of scraping teeth 58 may be configured as saw-toothed, or other shapes 60 well known to those of ordinary skill in the art. Also, it is foreseeable that in other embodiments, the device 18 may be constructed such that wmax-inner 49 is equal to wmax-outer 55. Similarly, it is foreseeable that in other embodiments w1, w2, w3, w4, wmax-inner 49, and wmax-outer 55 are all equal. Similarly, the present invention may be embodied with more than two scraping blades.

Before describing the floss holding assembly 62, several additional features of the scraper head 33 are described.

One problem commonly associated with prior art tongue scrapers is that in use, they splatter scraped debris 300 on the user as they are pulled across the tongue 19. These products oftentimes soil the clothing of the person using the product, and splatter anything in the vicinity, such as bathroom mirrors, with debris 300.

Figure 8:
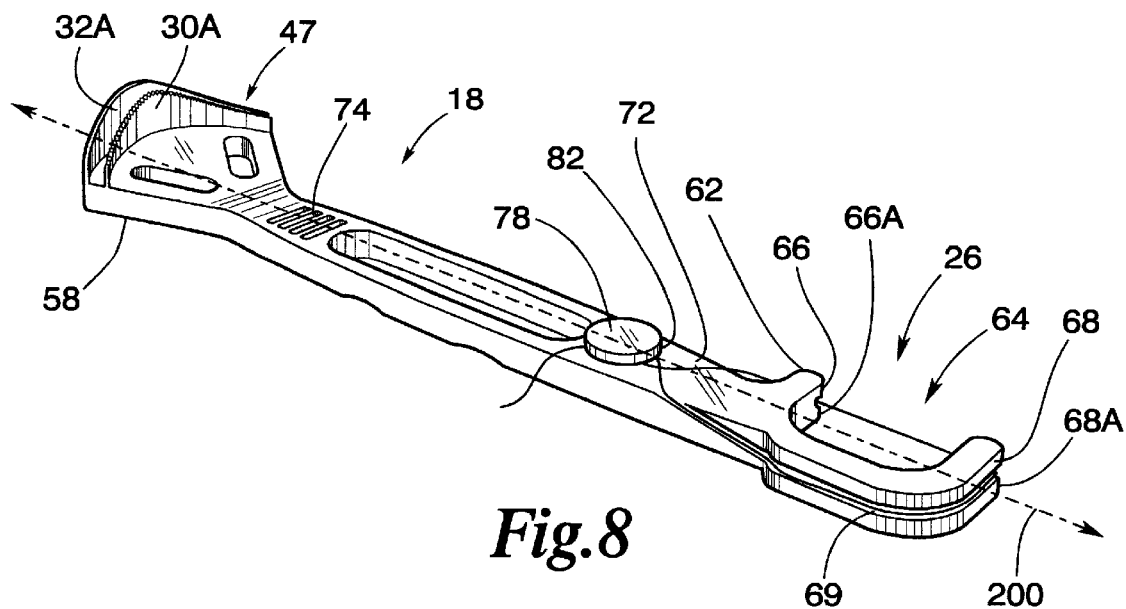
FIG. 8 is the same view as FIG. 1, with additional reference numbers.

The present device 18 avoids these problems by the way in which the blades 30,32 are configured, operate, and function. As seen in FIG. 9, the debris 300 scrapped by the blades 30,32 builds up, or accumulates, in front of the front side 32A of the smooth edged outer scraper blade 32, and the front side 30A of the toothed edged inner scraper blade 30 (FIG. 8). Accumulation of the debris 300 continues to build in front of the front sides 30A,32A of the blades 32,30, as they are pulled (scraped or dragged) across the surface of the tongue 19A. The accumulating debris 300 is seen in FIG. 9. There is little to no splattering of scraped debris 300 because the blades 30,32 are both curved (as seen in FIGS. 1 and 2), which fosters the gathering and collecting of debris 300, which prevents the spraying/splattering of debris. This curvature of the blades 30,32 may be described as generally U-shaped, or substantially V-shaped, as seen in FIGS. 1–4. Further, the blades 30,32 may be embodied to be at a substantially ninety degree angle with the scraper head flat surface 46. Such an angle promotes the clean scraping of debris 300 off the surface of the tongue 19A, and this, combined with the U-shaped curvature of the scraper blades 30,32, provides thorough cleaning of the tongue surface 19A, while simultaneously controlling the splattering of debris 300.

It is noted that in other embodiments, the blades 30,32 may be at angles other than substantially ninety degrees with the scraper head flat surface 46. For example, they may folded toward the floss holding assembly 62, such that they are at an angle substantially less than ninety degrees with the scraper head flat surface 46.

Another aspect of proper oral hygiene is cleaning the farthest back portion 19B of the tongue 19, so as to remove deleterious debris 300 therefrom. The tongue's 19 tip is usually automatically and naturally cleaned by the simple acts of talking, eating, chewing, and drinking fluids. However, the tongue's farthest back portion (or lower portion) 19B, has great amounts of bacteria and debris 300 buildup, because this region of the tongue 19 receives none of these natural cleaning benefits. As described below, the present device 18 is able to clean the tongue's 19 farthest back portion 19B without causing the user 100 to suffer from the gag reflex, i.e., a regurgitative spasm in the throat in response to an object introduced into the throat.

Cleaning the farthest back portion 19B of the tongue 19 is possible because of the width configuration of the toothed edged inner scraper blade 30, and the width configuration of the smooth edged outer scraper blade 32, as well as the U-shaped curved side 44 and associated curved edge 42 of the scraper head 33.

Figure 6:
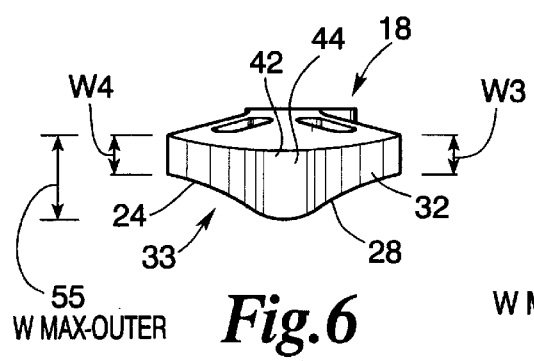
FIG. 6 is a left side elevational view of the tongue and tooth cleaning device.

As described above, w1 equals w2 as seen in FIG. 7, reaching a maximum at wmax-inner 49. Similarly w3 equals w4, reaching a maximum at wmax-outer 55 as seen in FIG. 6. Such a configuration minimizes the gag reflex, because as the device 18 is dragged across the tongue, the wmax-inner 49 portion of the toothed edged inner scraper blade 30, and the wmax-outer 55 portion of the smooth edged outer scraper blade 32 pass over the farthest back portions of the tongue 19B, as seen in FIG. 9, while the remainder of the blades 30,32 do not reach the farthest back portion 19B. Thus, such a configuration ensures that wmax-inner 49 and wmax-outer 55 reach the farthest back portion 19B of the tongue 19, thus abrogating the necessity of having to position the whole of the scraping blades 30, 32 into the farthest back portion 19B of the tongue 19. This thus allows the farthest back portion 19B of the tongue to be scraped and cleaned without the user 100 gagging.

Another advantage of device 18 is that the natural contour of the tongue 19 of the user 100 is in registry with the blades 30,32 during the scraping process. That is, the toothed edged inner scraper blade 30 has widths w1 and w2 that increase to a wmax-inner 49, and the smooth edged outer scraper blade 32 has widths w3 and w4 that increase to a wmax-outer 55. These wmax-inner 49 and wmax-outer portions of the scraping blades 30,32 are in registry with the natural contour of the surface of the tongue 19A, thus providing thorough cleaning when the device 18 is scraped across the user's 100 tongue 19.

At the other end of the handle 22, opposite the scraper head 33, is a floss holding assembly 62, as seen in FIGS. 1–4. The floss holding assembly 62 has fork-shaped tines 64 protruding therefrom. The fork-shaped tines 64 comprise a proximal tine 66 and the distal tine 68. The proximal tine 66 and the distal tine 68 each define a floss holding groove 69 for holding a piece of dental floss (tape) 70 therein. The forked shaped times 64 and their associated end tips (designated 66a and 68a) point in the direction of the X-axis, as shown in FIGS. 3, 4, and 8. The X-axis is perpendicular to the longitudinal axis 200 of the device 18, as seen in FIGS. 3, 4, and 8. It is also noted that in such a configuration, the fork-shaped tines 64 are coplanar (in the same plane) with the plane that passes lengthwise through the handle 22 and the longitudinal axis 200 of the device 18, as seen in FIGS. 1, 5, and 8. Further, the end tips designated 66a and 68a, and associated fork-shaped tines 64 point in a direction that is perpendicular to the longitudinal axis 200 of the device 18 in such a configuration. This is shown in FIGS. 1, 3, 5 and 8.

It is noted that the device 18 may be embodied and configured such that the forked shaped tines 64 point in a direction opposite to the direction in which they point in FIGS. 1, 3, and 4, or in any of the directions therebetween.

The scraper head 33 is at an angle from the longitudinal axis 200 of the device, such that it is bent towards the bottom surface 72 of the handle 22, as seen in FIGS. 1, 5. The bend facilitates the scraping process, that is it makes the device 18 easier to handle and use.

Figure 7:
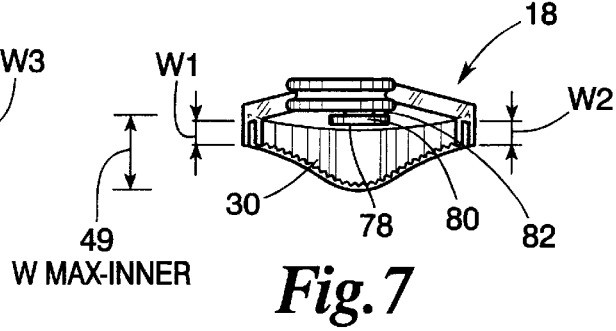
FIG. 7 is a right side elevational view of the tongue and tooth cleaning device.

Protruding from the bottom surface 72 of the handle 22 is a wrapping post 78, the wrapping post having a lesser diameter portion 82 (shown in FIGS. 5 and 7). The lesser diameter portion 82 is located at the region where the wrapping post 78 is connected to the bottom surface 72 of the handle 22. The wrapping post 78 has a greater diameter portion 80, separated a distance away from the bottom surface 72 of the handle 22, by the lesser diameter portion 82, as shown in FIGS. 5 and 7. Also, the bottom surface 72 of the handle 22 has a gripping surface 74 for providing the user with a good grip on the device 18 when using the device 18. The top surface 84 of the handle 22 may be embodied to have grooves 86, for accommodating the user's 100 hand, the grooves 86 shown in FIG. 2.

To use the device 18, the user 100 takes the device, holds the handle 22 and drags the scraper 28 across the surface of his or her tongue 19A (FIG. 9). In doing so, plaque and debris 300 are broken free from the tongue 19 and scraped off the surface of the tongue 19A, by the toothed edged inner scraper blade 30 and smooth edged outer scraper blade 32. The device may then be rinsed with water or otherwise cleaned. Next, a piece of dental floss 70 (or dental tape, or other strand-like material well known to those of ordinary skill in the art) is first wound around the lesser diameter portion 82 of the wrapping post 78, then strung through the holding groove 69 in the proximal tine 66 and the distal tine 68, and pulled taught by the user 100. While maintaining tension in the floss 70, the floss 70 is then again wrapped around the lesser diameter portion 82 of the wrapping post 78. The floss 70 is thus held taught between the fork-shaped tines 64. The user 100 may then floss the spaces 21 between his or her teeth 17. The floss 70 may then be discarded. Alternatively, the user 100 may first floss, and then scrape the surface of his or her tongue 19A with the device 18.

The device 18 may be constructed of plastics, metals, composites, nylons, and other materials well known to those of ordinary skill in the art. It may be molded and formed in the form of a unitary body, that is from a single piece of material or blank, as the device 18 is shown in FIGS. 1–7. It may also be made of constituent parts, that is the handle, the scraper head, and the flossing assembly may be independent parts that are then affixed to one another by means well known to those of ordinary skill in the art. All of this may be accomplished by means and methods well known to those of ordinary skill in the art.

It is to be understood that various changes in the details, parts, materials, steps and arrangements, which have been herein described and illustrated in order to describe the nature of the invention, may be made may be made by those skilled in the art within the principles and scope of the present invention. While an embodiment of the present invention has been described in detail, that has been done for purposes of illustration, not limitation.

What is claimed:

1. A device for cleaning the surface of a tongue comprising:
   a handle having a scraping end, the scraping end having a scraper, the scraper for removing debris from the tongue when scraped along the tongue, the handle having a length and defining a longitudinal axis that passes through the length thereof,
   the handle further comprising a bottom surface comprising a gripping surface and floss wrapping post,
   the handle further comprising a top surface that defines grooves, the gripping surface and the grooves for increasing the degree of grippability of the device when in use; and
   a flossing assembly joined with the handle at the end of the handle opposite the scraping end, wherein the flossing assembly comprises tines having grooves through which floss is stringable, and
   a wrapping post protruding from the bottom surface of the handle, the floss stringable through the grooves in the tines and wrappable around the wrapping post.

2. The device according to claim 1 wherein the scraper further comprises:
   a scraper head, the scraper head having: a plurality of scraper blades, wherein the plurality of scraper blades includes:
   a toothed edged inner scraper blade for disturbing debris on the tongue; and
   a smooth edged outer scraper blade for scraping the debris off the tongue, and wherein the toothed edged inner scraper blade and the smooth edged outer scraper blade are proximate to one another.

3. The device according to claim 2 wherein the scraper head has a scraper head flat surface from which the toothed edged outer scraper blade and smooth edged inner scraper blade protrude, and wherein the toothed edged outer scraper blade makes a substantially ninety degree angle with the scraper head flat surface, and the and the smooth edged inner scraper blade makes a substantially ninety degree angle with the scraper head flat surface, so that the debris is scraped from the tongue without splattering.

4. The device of claim 2 wherein the scraper head further comprises a first edge extending along a first side thereof, a second edge extending a second side thereof, and a curved edge extend along a curved side thereof, the curved side extending between the first side and the side edge.

5. The device according to claim 3 wherein the scraper head further comprises a first edge extending along a first side thereof, a second edge extending along a second edge thereof, and a curved edge extending along a curved side thereof, the curved side extending between the first side and the second side, wherein the curved side has a U-shaped configuration, the U-shaped configuration is for preventing the gag reflex in a user of the device to be triggered when the scraper head is dragged across the user's tongue.

6. The device of claim 4 having a scraper head flat surface defined by the first edge, the second edge, and the third edge, the toothed edged inner scraper blade and the smooth edged outer scraper blade protrude from the scraper head flat surface.

7. The device of claim 6 wherein the toothed edged inner scraper blade has a width that indicates the amount the toothed edged inner scraper blade protrudes from the scraper head flat surface, and the smooth edged outer scraper blade has a width that indicates the amount the smooth edged out scraper blade protrudes from the scraper head flat surface, and wherein the width of the toothed edged inner scraper blade and the width of the smooth edged outer scraper blade protrude form the scraper head flat surface is equal.

8. The device of claim 6 wherein the smooth edged outer scraper blade has a width that increases from the first edge of the first side of the device, and wherein as the smooth edged outer scraper blade approaches the longitudinal axis of the device, the width reaches a maximum outer blade protrusion at the point where the longitudinal axis passes through the smooth edged outer scraper blade, and then the width of the smooth edged outer scraper blade decreases from the maximum outer blade protrusion, as the smooth edged outer scraper blade approaches the second edge of the second side of the device.

9. The device of claim 8 wherein the toothed edged inner scraper blade has a width that increases from the first edge of the first side of the device, and wherein as the toothed edged inner scraper blade approaches the longitudinal axis of the device, the width reaches a maximum inner blade protrusion at the point where the longitudinal axis passes through the toothed edged inner scraper blade, and then the width of the toothed edged inner scraper blade decreases from the maximum inner blade protrusion, as the toothed edged inner scraper blade approaches the second edge of the second side of the device.

10. The device of claim 9 wherein the maximum outer blade protrusion of the smooth edged outer scraper blade is greater than the maximum inner blade protrusion of the toothed edged inner scraper blade, so that when the scraper is pulled over the tongue, the toothed edged inner scraper blade breaks up and dislodges debris and the smooth edged outer scraper blade scraps the debris off the tongue, and wherein the maximum inner blade protrusion and maximum outer blade protrusion are contoured so as to be in registry with the natural contour of the surface of the tongue.

11. The device of claim 2 wherein the toothed edged inner scraper blade comprises a plurality of individual scraping teeth, and the scraper head is at an angle to and bent towards the bottom surface of the handle, and wherein the device is formed as a unitary body, and is constructed from materials selected from the group consisting of: plastics, metals, composites, and combinations thereof.

12. A tongue and tooth cleaning device for cleaning a user's tongue and teeth comprising:
   a handle having a scraping end, the scraping end having a scraper, the scraper for removing debris from the tongue when scraped along the tongue,
   the handle further comprising a bottom surface comprising a gripping surface,
   the handle further comprising a top surface that defines grooves, the gripping surface and the grooves for increasing the grippability of the device,
   and wherein the scraper further comprises:
      a scraper head having:
         a toothed edged inner scraper blade for disturbing debris on the tongue;
         a smooth edged inner scraper blade for scraping debris off the tongue; and wherein the device further comprises:
            a flossing end of the handle opposite to the scraping end, the flossing end having a floss holding assembly, the floss holding assembly having fork-shaped tines for holding floss therebetween; the handle defining a longitudinal axis along the length thereof and the fork-shaped tines pointing in a direction perpendicular to the longitudinal axis defined by the handle.

13. The device of claim 12 wherein the scraper further comprises a scraper head flat surface defined by a first edge extending along a first side thereof, a second edge extending along a second side thereof, and a curved edge extending along a curved side thereof, the curved side extending between the first side and the second side, the toothed edged inner scraper blade and smooth edged outer scraper blade each extending from the first edge to the second edge, and each being curved such that the curvature of the toothed edged inner scraper blade and the smooth edged outer scraper blade mimic the curvature of the curved side of the scraper head, so that as the toothed edged inner scraper blade and smooth edged outer scraper blade gather debris as they are dragged across a surface of the tongue.

14. The device of claim 12 wherein the scraper head flat surface has protruding therefrom the toothed edged inner scraper blade and the smooth edged outer scraper blade, such that smooth edged outer scraper blade has a width that increases as it spans from the first side towards the longitudinal axis, reaching a maximum smooth edged outer blade protrusion, the width of the smooth edged outer scraper blade then decreases until the smooth edged outer scraper blade reaches the second side, and the toothed edged inner scraper blade has a width, the increases as it spans from the first side towards the longitudinal axis, reaching a maximum inner blade protrusion, the width of the toothed edged inner scraper blade then decreases until the toothed edged inner scraper blade reaches the second side.

15. A tooth and tongue cleaning device comprising:
   a handle having a scraping end and a flossing end, the scraping end having a scraper, the scraper for removing debris from the tongue when scraped along the tongue, and wherein the scraper further comprises a scraper head comprising:
      a toothed edged inner scraper blade for disturbing debris on the tongue; and
      a smooth edged outer scraper blade for scraping the debris off the tongue; and wherein the flossing end further comprises:
         a flossing assembly end positioned on the handle opposite to the scraping end, the flossing end for holding floss, the handle having a length and defining a longitudinal axis that passes through the length thereof, and wherein the flossing end comprises a floss holding assembly, and wherein the floss holding assembly comprises fork-shaped tines that point in a direction perpendicular to the longitudinal axis of the handle, and the fork-shaped tines comprise a proximate tine and a distal tine, the distal tine and the proximate tine each having a groove for holding floss therein, and the handle has a bottom surface and has protruding therefrom a floss wrapping post which floss is wrappable about, the floss is then stringable through the groove in the distal tine and the groove in the proximate tine, and then wrappable around the floss wrapping post again so that the floss is held taught.

16. The device of claim 15 wherein the scraper is bent towards at an angle towards the bottom surface of the handle, and wherein the device is molded in the form of a unitary body and constructed from at least one of the materials selected from the group consisting of: plastics, metals, and composites.

17. The device of claim 15 wherein the handle further comprises a bottom surface comprising a gripping surface, and the handle further comprising a top surface that defines grooves, the gripping surface and the grooves for increasing the degree to which the device can be gripped when in use.

18. A tooth and tongue cleaning device comprising:

a handle having a scraping end and a flossing end, the scraping end having a scraper, the scraper for removing debris from the tongue when scraped along the tongue, and wherein the scraper further comprises a scraper head comprising:

a toothed edged inner scraper blade for disturbing debris on the tongue; and a smooth edged outer scraper blade for scraping the debris off the tongue; and wherein the flossing end further comprises:

a flossing assembly end positioned on the handle opposite to the scraping end, the flossing end for holding floss, the handle having a length and defining a longitudinal axis that passes through the length thereof, and wherein the flossing end comprises a floss holding assembly, and wherein the floss holding assembly comprises fork-shaped tines that point in a direction perpendicular to the longitudinal axis of the handle, and the fork-shaped tines comprise a proximate tine and a distal tine, the distal tine and the proximate tine each having a groove for holding floss therein, and the handle has a bottom surface and has protruding therefrom a floss wrapping post which floss is wrappable about, the floss is then stringable through the groove in the distal tine and the groove in the proximate tine, and then wrappable around the floss wrapping post again so that the floss is held taught, and wherein the floss wrapping post has a lesser diameter portion where it is connected to the bottom side of the handle, and a greater diameter portion separated a distance away from the bottom side of the handle, so that the floss is wrappable about the lesser diameter portion.

19. A tooth and tongue cleaning device comprising:

a handle having a scraping end and a flossing end, the scraping end having a scraper, the scraper for removing debris from the tongue when scraped along the tongue, and wherein the scraper further comprises a scraper head comprising:

a toothed edged inner scraper blade for disturbing debris on the tongue; and a smooth edged outer scraper blade for scraping the debris off the tongue; and wherein the flossing end further comprises:

a flossing assembly end positioned on the handle opposite to the scraping end, the flossing end for holding floss, the handle having a length and defining a longitudinal axis that passes through the length thereof, and wherein the flossing end comprises a floss holding assembly, and wherein the floss holding assembly comprises fork-shaped tines that point in a direction perpendicular to the longitudinal axis of the handle, and the fork-shaped tines comprise a proximate tine and a distal tine, the distal tine and the proximate tine each having a groove for holding floss therein, the handle has a bottom surface and has protruding therefrom a floss wrapping post which floss is wrappable about, the floss is then stringable through the groove in the distal tine and the groove in the proximate tine, and then wrappable around the floss wrapping post again so that the floss is held taught, and wherein the bottom surface of the handle has a gripping surface, so that the handle is grippable by a user when using the device.

20. A method of cleaning a tongue comprising the acts of:

providing a device having a handle having a scraper head at an end thereof;

providing the scraper head with:

a toothed edged inner scraper blade for disturbing debris on the tongue;

a smooth edged inner scraper blade adjacent to the toothed edged inner scraper blade for scraping debris off the tongue; and the method further comprising the acts of:

dragging the scraper head across a surface of the tongue to remove debris therefrom, and providing the smooth edged outer scraper blade and the toothed edged inner scraper blade with a curved configuration for gathering debris as they are dragged over a user's tongue, and, providing the other end of the handle with a floss assembly, wherein the floss assembly comprises a proximal and distal tine, and wherein the handle defines a longitudinal axis along the length thereof, and wherein the proximal tine and the distal tine point in a direction perpendicular to the longitudinal axis of the handle.

21. The method of claim 20 further comprising the acts of providing the handle with a bottom surface comprising a gripping surface, and further providing the handle with a top surface that defines grooves, the gripping surface and the grooves for increasing the grippability of the device.

22. A tooth and tongue cleaning device comprising:

a handle having a scraping end and opposite thereto a flossing end, the scraping end having a scraper, the scraper for removing debris from the tongue when scraped along the tongue, and wherein the scraper further comprises a scraper head comprising:
a toothed edged inner scraper blade for disturbing debris on the tongue; and
a smooth edged outer scraper blade for scraping the debris off the tongue; and wherein the flossing end further comprises:
   a flossing assembly end positionable on the handle opposite to the scraping end, the flossing end for holding floss,
   the handle further comprising a bottom surface comprising a gripping surface and having a floss wrapping post protruding therefrom, the diameter of the floss wrapping post increasing the farther the floss wrapping post extends from the handle,
   the handle further comprising a top surface defining grooves, the gripping surface and the grooves for increasing the grippabilty of the device,
   wherein the handle defines a longitudinal axis passing through the length thereof, and wherein the flossing end comprises a floss holding assembly,
   and wherein the floss holding assembly comprises fork-shaped tines that point in a direction perpendicular to the longitudinal axis of the handle, the fork-shaped tines comprise a proximal tine and a distal tine, the distal tine and the proximal tine, the floss wrappable around the floss wrapping post, stringable through the grooves in the fork-shaped tines and wrappable around the floss wrapping post again.

23. The tongue and tooth cleaning device of claim 22 wherein the device is molded in the form of a unitary body and constructed from at least one of the materials selected from the group consisting of: plastics, metals, and composites.

* * * * *